United States Patent [19]

Bremer et al.

[11] 4,120,876

[45] Oct. 17, 1978

[54] PREPARATION OF MALEIC ANHYDRIDE FROM FOUR-CARBON HYDROCARBONS

[75] Inventors: Noel J. Bremer, Kent; James F. White, Akron; Ernest C. Milberger, Solon, all of Ohio

[73] Assignee: Standard Oil Company, Cleveland, Ohio

[21] Appl. No.: 733,739

[22] Filed: Oct. 19, 1976

[51] Int. Cl.$^2$ .......................................... C07D 307/60
[52] U.S. Cl. .............................................. 260/346.75
[58] Field of Search .................. 260/346.8 A, 346.75

[56] References Cited

U.S. PATENT DOCUMENTS 3,992,419  11/1976  Otaki et al. ................. 260/346.8 A Primary Examiner—Henry R. Jiles
Assistant Examiner—Bernard Dentz
Attorney, Agent, or Firm—Gwenetta Douglas Hill; Herbert D. Knudsen; Larry W. Evans

[57] ABSTRACT

Maleic anhydride is produced by the oxidation of n-butane, n-butenes, 1,3-butadiene or mixture thereof with molecular oxygen in the vapor phase in the presence of a catalytic oxide of molybdenum, phosphorus, arsenic, oxygen, and at least one element selected from the group consisting of Sn, rare earth metal, Zr, Rh, Mn, Re, Ru, Cu, Pb, Zn, Ti and Cr, Nb, Al, Ga, and alkaline earth metal.

13 Claims, No Drawings

PREPARATION OF MALEIC ANHYDRIDE FROM FOUR-CARBON HYDROCARBONS

BACKGROUND OF THE INVENTION

French Pat. No. 1,601,955 teaches use of a catalyst having the composition $AO_3\text{-}B_2O_5\text{-}M_2O_5\text{-}N_xO\text{-}R_2O$ wherein A is Cr, Mo, W or U; B is V or Nb; M is P, As, Sb or Bi, N is Cu, Ag, Fe, Co or Ni; R is Li, Na, K, Cs or Rb. Preferred composition is 15–55 atomic %A, 30–70% B, 0–15% M, 0.1–20% N, and 0–15% R.

The present invention is a result of a search for more efficient catalysts for use in the oxidation of four-carbon hydrocarbons to produce maleic anhydride.

The catalysts employed in the present invention are unexpectedly advantageous in the production of maleic anhydride from n-butane, n-butenes and 1,3-butadiene.

SUMMARY OF THE INVENTION

It has now been discovered according to the present invention in the process for the production of maleic anhydride by the oxidation of n-butane, n-butenes, 1,3-butadiene or mixture thereof, with molecular oxygen in the vapor phase at a reaction temperature of about 250° C. to about 600° C. in the presence of a catalyst, and optionally in the presence of steam, the improvement which comprises using as a catalyst a catalyst described by the formula

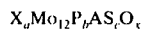

$$X_a Mo_{12} P_b As_c O_x$$

wherein X is at least one element selected from the group consisting of Sn, rare earth metal, Zr, Rh, Mn, Re, Ru, Cu, Pb, Zn, Ti, and Cr, Nb, Al, Ga and alkaline earth metal; and
wherein a is a positive number less than about 20;
 b and c are numbers from 0.001 to 10;
 x is the number of oxygen required by the valence states of the other elements present.

Especially high yields and selectivities of maleic anhydride are obtained from four-carbon hydrocarbons in an efficient, convenient, and economical manner at a relatively low temperature. The exotherm of the reaction is low, thereby, allowing easy reaction control.

The most significant aspect of the present invention is the catalyst employed. The catalyst may be any of the catalysts delineated by the above formula. Preferred catalysts within the formula are described wherein a is a positive number less than about 12, catalysts wherein b is 0.01 to 5, and catalysts wherein c is 0.01 to 5. Highly desirable results are obtained wherein b is 0.5 to 1.5 and c is 0.1 to 1.0 Preferred catalysts are described wherein each element delineated by X is separately incorporated into the catalyst. Especially preferred catalysts are described wherein X is copper in combination with at least one of the remaining elements also delineated by X.

The methods of preparing the catalysts of the present invention may vary widely. A number of techinques are known to those skilled in the art. Methods of catalyst preparations such as coprecipation, evaporative drying, or oxide mixing, followed by calcining the resulting catalysts may be successively employed.

The preferred procedure of this invention involves preparing the catalysts in an aqueous slurry or solution of compounds containing molybdenum, arsenic and/or phosphorus, adding the remaining components; evaporating this aqueous mixture; and calcining the resulting catalysts. Suitable molybdenum compounds that may be employed in the preparation of the catalysts delineated by the above formula include molydbenum trioxide, phosphomolybdic acid, molybdic acid, and ammonium heptamolybdate. Suitable phosphorus compounds that may be employed in the preparation of the catalysts include orthophosphoric acid, metaphosphoric acid, triphosphoric acid, and phosphorus halides or oxyhalides. The remaining components of the catalysts may be added as oxide, acetate, formate, sulfate, nitrate, carbonate, halide and oxyhalide.

The best results are obtained by refluxing phosphoric acid, ammonium arsenate, and molybdenum trioxide or ammonium heptamolybdate in water for about 0.5 to 3 hours, however, commercial phosphomolybdic acid may be effectively utilized; adding compounds containing elements delineated by X to the aqueous slurry and boiling to a thick paste; and drying the mixture at 110° C. to 120° C. in air and calcining the resulting catalysts.

Calcination of catalysts of the invention is ususally accomplished by heating the dry catalytic components at a temperature of about 300° C. to 700° C.; preferred calcination is accomplished at a temperature of 325° C. to 450° C. The hydrocarbon reacted may be n-butane, n-butenes, 1,3-butadiene or mixture thereof. Preferred is the use of 1,3-butadiene or a mixture of hydrocarbons that are produced in refinery streams. The molecular oxygen is most conveniently added as air, but synthetic streams containing molecular oxygen are also suitable. In addition to the hydrocarbon and molecular oxygen, other gases may be added to the reactant feed. For example, stream or nitrogen could be added to the reactants.

The ratio of the reactants may vary widely and are not critical. The ratio of the hydrocarbon to molecular oxygen may range from about 2 to about 30 moles of oxygen per mole of hydrocarbon. Preferred oxygen ratios are about 4 to about 20 moles per mole of hydrocarbon.

The reaction temperature may vary widely and is dependent upon the particular hydrocarbon and catalyst employed. Normally, temperatures of about 250° C. to about 600° C. are employed with temperatures of 250° C. to 450° C. being preferred.

The catalyst may be used alone or a support could be employed. Suitable supports include silica, alumina, Alundum, silicon carbide, boron phosphate, zirconia, and titania. The catalysts are conveniently used in a fixed-bed reactor using tablets, pellets or the like or in a fluid-bed reactor using a catalyst preferably having a particle size of less than about 300 microns. The contact time may be as low as a fraction of a second or as high as 20 seconds or more. The reaction may be conducted at atmospheric, superatmospheric or subatmospheric pressure.

Excellent results are obtained using a coated catalyst consisting essentially of an inert support material having a diameter of at least 20 microns and an outer surface and a continuous coating of said active catalyst on said inert support strongly adhering to the outer surface of said support.

By use of these coated catalysts in the reaction to produce maleic anhydride, a very low exotherm is realized allowing for better control of the reaction. High single pass yields are exhibited and the elimination of undesirable byproducts is obtained.

The special coated catalyst consists of an inner-support material having an outside surface and a coating of the active catalytic material on this outside surface. These catalysts can be prepared by a number of different methods.

The support material for the catalyst forms the iner core of the catalyst. This is an essentially inert support and may have substantially any particle size or shape although a diameter of greater than 20 microns is preferred. Especially preferred in the present invention for use in a commercial reactor are those supports which are spherical and which have a diameter of about 0.2 cm. to about 2 cm. Suitable examples of essentially inert support materials include: Alundum, silica, alumina, alumina-silica, silicon carbide, titania and zirconia. Especially preferred among these supports are Alundum, silica, alumina and alumina-silica.

The catalysts may contain essentially any proportions of support and catalytically active material. The limits of this relationship are only set by the relative ability of the catalyst and support material to accommodate each other. Preferred catalysts contain about 10 to about 100 percent by weight of catalytically active material based on the weight of the support.

The preparation of these coated catalysts can be accomplished by various techniques. The basic method of preparing these catalysts is to partially wet the support material with a liquid. The support should not be wet on the outside surface of the total mass. It should appear to be dry to the touch. If the support is wet, then the active catalytic material may agglomerate into separate aggregates when coating of the support is attempted. These partially wet supports are then contacted with a powder of the catalytically active material and the mixture is gently agitated until the catalyst is formed. The gentle agitation is most conveniently conducted by placing the partially wet support in a rotating drum or jar and adding the active catalytic material. This is very economically done.

Using the catalysts of the invention in the preparation of maleic anhydride, excellent yields are obtained in a convenient reaction with low amounts of byproducts.

SPECIFIC EMBODIMENTS

Examples 1 to 18: Preparation of Maleic Anhydride Using Various Catalysts of the Invention

Examples 1 to 3

Various catalysts of the invention were prepared as follows:

Example 1

$Mo_{12}P_{1.32}As_{0.5}Cu_{0.25}O_x$

A slurry consisting of 317.8 grams of ammonium heptamolybdate, $(NH_4)_6Mo_7O_{24}\cdot 4H_2O$ and 1500 mls. of distilled water was boiled with stirring. To this slurry was added 11.91 grams of ammonium arsenate, $NH_4H_2AsO_4$, and heating was resumed for 20 minutes; the color was white. Upon the addition of 7.5 grams of copper acetate, the color changed to light blue. To this mixture was added 22.8 grams of phosphoric aicd, $H_3PO_4$ (85% solution), and 10 minutes later 7.5 grams of hydrazine were added to give a dark blue solution which was evaporated to a thick paste, dried overnight at 100° C. to 120° C. and ground and screened to less than 50 mesh. The resulting catalyst was calcined 1 hour at 371° C. in 40 mls/minute air.

Example 2

$Mo_{12}P_{1.32}As_{0.5}Cu_{0.20}Cr_4O_x$

A slurry was prepared consisting of 105.9 grams of ammonium heptamolybdate, 700 mls. of 60° C. distilled water and 3.97 grams of ammonium arsenate as solution in 25 mls. water; a white precipitate formed which was heated to boiling for 45 minutes. To this mixture was added 15.2 grams of chromium oxide; 15 minutes later 2.4 grams of copper acetate were added; and ½ hour later 7.6 grams of 85% phosphoric acid was added. The solution was boiled to a thick paste; dried in an oven overnight at 110° to 120° C.; and ground and screened to less than 50 mesh size. Calcination was the same as described in Example 2.

Example 3

25% $Mo_{12}P_{1.32}As_{0.5}Cu_{0.20}Cr_4O_x$ + 75% Alundum (coated)

This catalyst was prepared in the same manner described in Example 3, except the dry catalytic particles were coated on ⅛ inch SA5223 Alundum balls by taking 50 grams of Alundum, partially wetting the Alundum with 1.8 grams of water and adding 16.7 grams of active catalyst prepared above in five equal portions. During and after each addition, the Alundum was rolled in a glass jar. The powder was evenly coated onto the surface of the Alundum and the final product was dried. The hard uniform coated catalyst was obtained that consisted of the Alundum support with the continuous, strongly adhering coating of the active catalyst. The catalyst was then calcined for 2 hours at 371° C. in 40 ml/min. air.

Example 4 to 18

Preparation of Maleic Anhydride from 1,3-butadiene

A portion of the catalyst particles prepared in accordance with Examples 1 to 3 were charged to a 20 cc. fixed-bed reactor equipped with a 1.02 cm. inside diameter stainless steel tube.

The reactor was heated to reaction temperature under a flow of air and a feed of 1,3-butadiene/air as indicated below was fed over the catalyst at an apparent contact time of 3 to 4 seconds and the performance evaluated by collecting and analyzing the products.

The results of these experiments appear in the TABLE below. The following definitions are used in measuring the carbon atoms in the feed and in the product:

% Single Pass Yield =
$$\frac{\text{Moles of Maleic Anhydride Recovered}}{\text{Moles of Hydrocarbon in the Feed}} \times 100$$

Total Conversion =
$$\frac{\text{Moles of Hydrocarbon Reacted}}{\text{Moles of Hydrocarbon in the Feed}} \times 100$$

% Selectivity =
$$\frac{\text{Single Pass Yield of Maleic Anhydride}}{\text{Single Pass Yield of Total Acid}} \times 100$$

TABLE

Preparation of Maleic Anhydride from 1,3-Butadiene Using Various Catalysts of the Invention

| Example | Catalyst | Feed Ratio Air/HC | Temp. °C Bath | Temp. °C Exotherm | Results, % Total Acid | Results, % Maleic Anhydride | Results, % Selectivity |
|---|---|---|---|---|---|---|---|
| 4  | $Mo_{12}P_{1.32}As_{0.5}Cu_{0.25}O_x$ | 25.20 | 263 | 270 | 6.41  | 4.56  | 71.11 |
| 5  | $Mo_{12}P_{1.32}As_{0.5}Cu_{0.25}O_x$ | 26.30 | 280 | 306 | 38.33 | 32.09 | 83.73 |
| 6  | $Mo_{12}P_{1.32}As_{0.5}Cu_{0.25}O_x$ | 26.58 | 294 | 389 | 60.19 | 50.16 | 83.33 |
| 7  | $Mo_{12}P_{1.32}As_{0.5}Cu_{0.25}O_x$ | 29.28 | 308 | 343 | 50.99 | 43.12 | 84.57 |
| 8  | $Mo_{12}P_{1.32}As_{0.5}Cu_{0.2}Cr_4O_x$ | 24.55 | 251 | 256 | 17.19 | 4.13  | 24.0  |
| 9  | $Mo_{12}P_{1.32}As_{0.5}Cu_{0.2}Cr_4O_x$ | 26.19 | 269 | 355 | 50.93 | 43.25 | 84.93 |
| 10 | $Mo_{12}P_{1.32}As_{0.5}Cu_{0.2}Cr_4O_x$ | 24.56 | 286 | 369 | 52.51 | 43.82 | 83.44 |
| 11 | $Mo_{12}P_{1.32}As_{0.5}Cu_{0.2}Cr_4O_x$ | 25.06 | 303 | 367 | 55.74 | 47.41 | 85.06 |
| 12 | $Mo_{12}P_{1.32}As_{0.5}Cu_{0.2}Cr_4O_x$ | 25.26 | 316 | 371 | 51.05 | 44.58 | 87.32 |
| 13 | 25% $Mo_{12}P_{1.32}As_{0.5}Cu_{0.2}Cr_4O_x$ + 75% Alundum (coated) | 23.77 | 303 | 320 | 50.71 | 44.23 | 87.22 |
| 14 | 25% $Mo_{12}P_{1.32}As_{0.5}Cu_{0.2}Cr_4O_x$ + 75% Alundum (coated) | 21.74 | 321 | 348 | 51.90 | 45.91 | 88.47 |
| 15 | 25% $Mo_{12}P_{1.32}As_{0.5}Cu_{0.2}Cr_4O_x$ (coated) | 25.05 | 336 | 388 | 46.98 | 39.36 | 83.78 |
| 16 | 25% $Mo_{12}P_{1.32}As_{0.5}Cu_{0.2}Cr_4O_x$ (coated) | 25.86 | 371 | 406 | 47.31 | 41.28 | 87.26 |
| 17 | 25% $Mo_{12}P_{1.32}As_{0.5}Cu_{0.2}Cr_4O_x$ (coated) | 24.84 | 386 | 413 | 46.30 | 42.55 | 91.89 |
| 18 | 25% $Mo_{12}P_{1.32}As_{0.5}Cu_{0.2}Cr_4O_x$ (coated) | 22.74 | 418 | 446 | 47.11 | 40.74 | 86.48 |

We claim:

1. In a process for the preparation of maleic anhydride by the oxidation of n-butane, n-butenes, 1,3-butadiene or mixture thereof with molecular oxygen in the vapor phase at a reaction temperature of about 250° C. to 600° C. in the presence of a catalyst, the improvement comprising using as a catalyst a catalyst of the formula $$X_a Mo_{12} P_b As_c O_x$$

wherein X is at least one element selected from the group consisting of Sn, rare earth metal, Zr, Rh, Mn, Re, Ru, Cu, Pb, Zn, Ti, Cr, Nb, Al, Ga, and alkaline earth metal; and
wherein
 a is a positive number less than about 20;
 b and c are numbers from 0.001 to 10;
 x is the number of oxygens required by the valence states of the other elements present.

2. The process of claim 1 wherein a is a positive number less than about 12.

3. The process of claim 1 wherein b is 0.01 to 5.

4. The process of claim 1 wherein c is 0.01 to 5.

5. The process of claim 1 wherein b is 0.5 to 1.5 and c is 0.1 to 1.0.

6. The process of claim 1 wherein X is copper.

7. The process of claim 1 wherein X is copper and chromium.

8. The process of claim 1 wherein 1,3-butadiene is reacted.

9. The process of claim 1 wherein the catalyst is coated on an inert support.

10. The process of claim 9 wherein the catalyst consists essentially of an inert support material having a diameter of at least 20 microns and an outer surface and a continuous coating of said active catalyst strongly adhering to the outer surface of said support.

11. The process of claim 10 wherein the active catalyst is about 10 to about 100 percent by weight of the inert support.

12. The process of claim 10 wherein the inert support is selected from the group consisting of silica, alumina, alumina-silica, silicon carbide, titania and zirconia.

13. The process of claim 10 wherein the particle size of the inert support is 0.2 cm. to 2 cm.